(12) United States Patent
Yin et al.

(10) Patent No.: US 10,827,952 B2
(45) Date of Patent: Nov. 10, 2020

(54) ELECTROCARDIOGRAPHIC BIOMETRIC AUTHENTICATION

(71) Applicants: Shihui Yin, Mesa, AZ (US); Jae-sun Seo, Tempe, AZ (US); Sang Joon Kim, Suwon-Si (KR); Chisung Bae, Suwon-Si (KR)

(72) Inventors: Shihui Yin, Mesa, AZ (US); Jae-sun Seo, Tempe, AZ (US); Sang Joon Kim, Suwon-Si (KR); Chisung Bae, Suwon-Si (KR)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 169 days.

(21) Appl. No.: 16/097,552

(22) PCT Filed: Apr. 28, 2017

(86) PCT No.: PCT/US2017/030269
§ 371 (c)(1),
(2) Date: Oct. 29, 2018

(87) PCT Pub. No.: WO2017/190089
PCT Pub. Date: Nov. 2, 2017

(65) Prior Publication Data
US 2019/0150794 A1    May 23, 2019

Related U.S. Application Data

(60) Provisional application No. 62/329,710, filed on Apr. 29, 2016.

(51) Int. Cl.
*G06K 9/00* (2006.01)
*A61B 5/117* (2016.01)
(Continued)

(52) U.S. Cl.
CPC ............ *A61B 5/117* (2013.01); *A61B 5/0452* (2013.01); *A61B 5/0456* (2013.01);
(Continued)

(58) Field of Classification Search
CPC ... A61B 5/117; A61B 5/04525; A61B 5/0452; A61B 5/7264; A61B 5/7246;
(Continued)

(56) References Cited

U.S. PATENT DOCUMENTS 9,466,362 B2    10/2016    Yu et al.
9,934,463 B2    4/2018    Seo et al.
(Continued)

FOREIGN PATENT DOCUMENTS

WO    2015039102        3/2015
WO    2018022821 A1    2/2018
WO    2018057749 A1    3/2018

OTHER PUBLICATIONS

Arteaga-Falconi, Juan Sebastian, Hussein Al Osman, and Abdulmotaleb El Saddik. "ECG authentication for mobile devices." IEEE Transactions on Instrumentation and Measurement 65.3 (2015): 591-600. (Year: 2015).*

(Continued)

*Primary Examiner* — Li Liu
(74) *Attorney, Agent, or Firm* — Fish & Richardson P.C.

(57) ABSTRACT

Methods, systems, and apparatus, including computer programs encoded on a computer storage medium, for obtaining an electrocardiographic (ECG) signal of a user; obtaining a feature vector of the ECG signal of the user with neural network based feature extraction. Comparing the feature vector of the ECG signal with a stored feature vector of a registered user. Authenticating the user in response to determining that a similarity of the ECG feature vector of the (Continued)

ECG signal and the stored ECG feature vector of the registered user exceeds a pre-defined threshold value.

17 Claims, 11 Drawing Sheets

(51) Int. Cl.
| | |
|---|---|
| *G06F 21/32* | (2013.01) |
| *H04L 29/06* | (2006.01) |
| *A61B 5/0452* | (2006.01) |
| *A61B 5/00* | (2006.01) |
| *H04W 12/06* | (2009.01) |
| *A61B 5/0456* | (2006.01) |
| *G06N 3/04* | (2006.01) |
| *G06N 3/08* | (2006.01) |

(52) U.S. Cl.
CPC ........ *A61B 5/04525* (2013.01); *A61B 5/7203* (2013.01); *A61B 5/7246* (2013.01); *G06F 21/32* (2013.01); *G06K 9/00885* (2013.01); *G06N 3/0454* (2013.01); *G06N 3/084* (2013.01); *H04L 29/06* (2013.01); *H04W 12/0605* (2019.01); *G06K 2009/00939* (2013.01); *H04L 63/0861* (2013.01)

(58) Field of Classification Search
CPC .............. A61B 5/7267; A61B 5/04012; A61B 5/0006; A61B 5/02438; A61B 5/0402; A61B 5/0456; A61B 5/681; G06K 2009/00939; G06K 9/00885; G06K 9/00536; G06K 9/00503; G06N 3/0454; G06N 20/00; G06N 3/04; G06N 3/08
See application file for complete search history.

(56) References Cited

U.S. PATENT DOCUMENTS

| | | |
|---|---|---|
| 2005/0281439 A1 | 12/2005 | Lange |
| 2014/0029660 A1 | 1/2014 | Bolstad et al. |
| 2014/0188770 A1* | 7/2014 | Agrafioti ................ A61B 5/117 706/13 |
| 2014/0364756 A1 | 12/2014 | Brockway et al. |
| 2016/0089047 A1* | 3/2016 | Jonnada ............... A61B 5/6801 600/516 |
| 2016/0293167 A1* | 10/2016 | Chen ....................... G10L 17/18 |
| 2016/0328644 A1* | 11/2016 | Lin .......................... G06N 3/08 |
| 2016/0352727 A1* | 12/2016 | Day ....................... A61B 5/0006 |
| 2017/0035327 A1* | 2/2017 | Yuen ........................ A61B 5/11 |
| 2017/0188971 A1* | 7/2017 | Liu ........................ A61B 5/0006 |
| 2017/0215806 A1* | 8/2017 | Bae ....................... A61B 5/7264 |
| 2017/0300815 A1 | 10/2017 | Seo |
| 2019/0080755 A1 | 3/2019 | Seo et al. |
| 2019/0087719 A1 | 3/2019 | Seo et al. |
| 2019/0147277 A1* | 5/2019 | Trigueiros Da Silva Cunha ........ G06F 21/32 |
| 2019/0164538 A1 | 5/2019 | Seo et al. |
| 2019/0244100 A1 | 8/2019 | Seo et al. |

OTHER PUBLICATIONS

Biel, et al., "ECG analysis: a new approach in human identification," IEEE Transactions on Instrumentation and Measurement, vol. 50, No. 3, pp. 808-812, 2001.
Chen, et al. "Compressing Neural Networks with the Hashing Trick". International Conference on Machine Learning, Lille, France, pp. 2285-2294, 19, 2015.
Choi, et al., "A PD Control-based QRS Detection Algorithm for Wearable ECG applications," EMBS, pp. 5638-5641, 2012.
Coutinho, et al., "One-lead ECG-based personal identification using Ziv-Merhav cross parsing," ICPR, pp. 3858-3861, 2010.
Han, et al. "Deep Compression: Compressing Deep Neural Networks with Pruning, Trained Quantization and Huffman Coding." (oral) International Conference on Learning Representations arXiv preprint arXiv:1510.00149, pp. 1-14, Dec. 2015.
Hatamian, et al. "A 100 MHz 40-tap programmable FIR filter chip," IEEE ISCAS, pp. 3053-3056, 1990.
Hinton, et al., "Reducing the dimensionality of data with neural networks," Science, vol. 313, No. 5786, pp. 504-507, 2006.
Israel, et al., "ECG to identify individuals," Pattern Recognition, vol. 38, No. 1, pp. 133-142, 2005.
Lourenco, et al., "Outlier detection in non-intrusive ECG biometric system," ICIAR, pp. 43-52, 2013.
Odinaka, et al., "ECG biometrics: A robust short-time frequency analysis," IEEE International Workshop on Information Forensics and Security (WIFS), pp. 1-6, 2010.
Page, et al., "Utilizing deep neural nets for an embedded ECG-based biometric authentication system," BioCAS, 2015, pp. 1-4, Oct. 22-24, 2015.
PCT International Search Report and Written Opinion in International Appln. No. PCT/US2017/030269, dated Jul. 18, 2017. 17 pages.
Shen, et al., "One-lead ECG for identity verification," EMBS, pp. 62-63, 2002.
Sufi, et al., "Polynomial distance measurement for ECG based biometric authentication," Security and Communication Networks, vol. 3, No. 4, pp. 303-319, 2010.
Wang, et al., "Analysis of human electrocardiogram for biometric recognition," EURASIP Journal of Advances in Signal Processing, Article ID 148658, 2008, Dec. 2007, 11 pages.
Xue, et al. "Restructuring of deep neural network acoustic models with singular value decomposition." INTERSPEECH. Jan. 2013. 5 pages.
Zhang, "A survey of sparse representation: algorithms and applications," IEEE Access, vol. 3, pp. 490-530, May 2015.

* cited by examiner

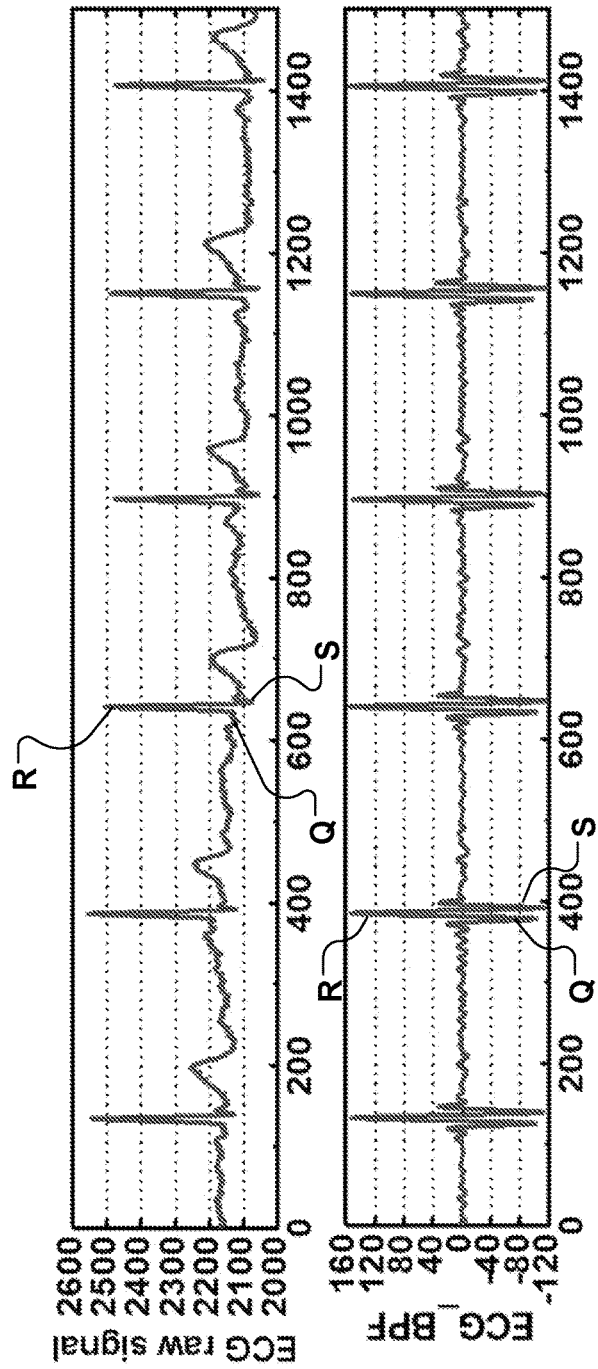

|  | Percentage of 0 weights in | | | | Lasso | | OMP | | Discard weights below some threshold | | |
|---|---|---|---|---|---|---|---|---|---|---|---|
|  | NN1 | NN2 | NN3 | NN4 | EER | FAR | EER | FAR | EER | FAR | Discard Ratio |
| 0.002 | 64.36% | 70.82% | 70.28% | 99.43% | 2.068% | 0.672% |  |  | 1.905% | 0.924% | 70% |
| 0.005 | 70.10% | 75.20% | 75.50% | 99.57% | 1.905% | 0.588% |  |  | 1.959% | 0.672% | 75% |
| 0.01 | 73.07% | 77.54% | 77.94% | 99.60% | 1.905% | 0.588% |  |  | 1.905% | 0.728% | 77% |
| 0.02 | 76.29% | 79.60% | 79.86% | 99.73% | 1.905% | 0.588% | 2.286% | 0.756% | 1.905% | 0.868% | 80% |
| 0.05 | 80.98% | 82.42% | 81.84% | 99.80% | 1.932% | 0.588% |  |  | 1.905% | 0.756% | 82% |
| 0.1 | 84.77% | 84.56% | 83.88% | 99.80% | 1.905% | 0.700% |  |  | 1.905% | 0.896% | 84% |
| 0.2 | 88.21% | 87.12% | 86.02% | 99.87% | 1.932% | 0.868% | 2.041% | 0.812% | 1.388% | 0.896% | 86% |
| 0.5 | 92.56% | 89.98% | 89.48% | 99.90% | 1.905% | 0.840% |  |  | 1.714% | 1.036% | 90% |

FIG. 8

ELECTROCARDIOGRAPHIC BIOMETRIC AUTHENTICATION

CROSS REFERENCE TO RELATED APPLICATIONS

This application is a U.S. National Phase Application of International Patent Application No. PCT/US2017/030269 entitled "ELECTROCARDIOGRAPHIC BIOMETRIC AUTHENTICATION", filed on Apr. 28, 2017, which claims the benefit of U.S. Provisional Application Ser. No. 62/329,710, entitled "ELECTROCARDIOGRAPHIC BIOMETRIC AUTHENTICATION FOR WEARABLE SYSTEMS FEATURING SPARSE MEMORY COMPRESSION" and filed Apr. 29, 2016, both of which are incorporated herein by reference in their entirety.

TECHNICAL FIELD

This invention is related to apparatus, systems, and methods for a low-power ECG-based biometric authentication engine for embedding in wearable devices. In particular, optimizing selective low-precision representation and sparsified weight memory compression allow reduction in computation and memory requirements of the apparatus, resulting in a small memory footprint and low power usage for real-time ECG authentication.

BACKGROUND

In the era of Internet of Things (IoT), a plethora of wearable devices will be integrated in our everyday life. Considering each individual's personal data that is locally stored and communicated wirelessly, secure measures to control access to such wearable devices are needed. Unlike traditional numerical or literal passwords, biometric authentication relies on unique physical characteristics (face, fingerprint, voice, iris, etc.) of each person with a non-intrusive interface. Among different biometrics, fingerprints have been most widely used in recent handheld products, but fingerprint authentication suffers from spoofing attacks as it does not require any liveness checks.

SUMMARY

Apparatus, systems, and methods for electrocardiographic (ECG)-based biometric authentication are described. ECG-based authentication is advantageous in that it has intrinsic liveness detection and cannot be easily spoofed as the ECG tracing depends on the detailed electrical activity of the heart. An ECG-based biometric hardware engine that consumes <100 µW and can be used together with existing fingerprint or voice recognition for further enhanced security in personal wearable devices. Ultra-low power consumption and small hardware footprint promote integration of the authentication engine into wearable devices that have small form factor and stringent battery constraints. Hardware optimization techniques include selective low precision, memory compression, and computation reduction. An implementation of an embodiment of this disclosure on Altera Arria-V FPGA as well as 65 nm CMOS ASIC (application-specific integrated circuits) demonstrate real-time ECG authentication that performs filtering, peak detection, and outlier removal, followed by feature extraction and identification using neural networks trained offline. The memory bottleneck of neural network weights is addressed by 4.2× weight compression by first finding the sparsest representation of the weight matrices and then compressing them. The authentication engine shows equal error rate (EER) of 0.149% and false acceptance rate (FAR) of 0% at false reject rate (FRR)=5% with only 36.8 kB of memory and 90 µW dynamic power consumption.

In general, innovative aspects of the subject matter described in this specification can be embodied in methods that include the actions of: obtaining an electrocardiographic (ECG) signal of a user; obtaining a feature vector of the ECG signal of the user with neural network based feature extraction; comparing the feature vector of the ECG signal with a stored feature vector of a registered user; authenticating the user in response to determining that a similarity of the ECG feature vector of the ECG signal and the stored ECG feature vector of the registered user exceeds a predefined threshold value. Other implementations of this aspect include corresponding systems, apparatus, and computer programs, configured to perform the actions of the methods, encoded on computer storage devices.

These and other implementations can each optionally include one or more of the following features.

In some implementations, obtaining the feature vector includes extracting features of the ECG signal using multiple parallel neural networks to obtain respective feature vectors, particular to each of the neural networks, and concatenating the respective feature vectors to provide the feature vector of the ECG signal.

Some implementations include the actions of: filtering the ECG signal with a finite impulse response filter to provide a filtered ECG signal; detecting R-peaks in the filtered ECG signal; and aligning segments of the ECG signal based on the detected R-peaks in the filtered ECG signal.

In some implementations, obtaining the feature vector includes the actions of: providing sets of aligned segments of the ECG signal to multiple parallel neural networks, each set of aligned segments of the ECG signal being provided to a respective one of the multiple parallel neural networks; extracting features from the sets of aligned segments using the multiple parallel neural networks to obtain respective feature vectors, particular to each of the neural networks; and concatenating the respective feature vectors to provide the feature vector of the ECG signal.

In some implementations, each of the sets of aligned segments of the ECG signal are filtered by a respective band-pass filter, each respective band-pass filter having a different pass band.

In some implementations, segments of at least one of the sets of aligned segments are aligned at ECG wave R-peak points, and segments of at least one other of the sets of aligned segments are aligned at ECG wave Q-points.

Some implementations include removing outlier data from the ECG data segments.

Some implementations include normalizing the ECG data segments.

In some implementations, at least one of the multiple parallel neural networks include a compressed layer weight matrix, the compressed layer weight matrix being a sparse approximation of a corresponding non-compressed layer weight matrix. In some implementations, the sparse approximation is a Lasso regression or an orthogonal matching pursuit. In some implementations, only the non-zero weights of the compressed layer weight matrix are stored in memory.

Some implementations include making features of a wearable device accessible to the user in response to authenticating the user.

In some implementations, the multiple neural networks each include an input layer and a hidden layer, where particular feature vector of each of the multiple neural networks is an output of the hidden layer of the respective neural network. In some implementations, the multiple neural networks each include a respective output layer during neural network training, and after training each respective output layer is discarded such that the particular feature vector of each of the multiple neural networks is a direct output of the hidden layer of the respective neural network.

In some implementations, comparing the feature vector of the ECG signal with the stored feature vector of the registered user includes determining a cosine similarity of the feature vector of the ECG signal and the stored feature vector of the registered user.

Another general aspect can be embodied in a wearable device that includes an authentication circuit, at least one processor, and a data store. The authentication circuit is configured to perform electrocardiographic authentication of a user. The authentication circuit includes an input configured to receive an electrocardiographic (ECG) signal of the user, noise reduction circuitry configured to filter the ECG signal, feature extraction configured to implement multiple parallel neural networks to obtain a feature vector of the ECG signal that represents features extracted from the ECG signal by the neural networks, similarity evaluation circuitry configured to determine a cosine similarity of the feature vector of the ECG signal with a stored feature vector of a registered user, and authentication circuitry configured to authenticate the user in response to determining the cosine similarity exceeds a pre-defined threshold value. The data store is coupled to the at least one processor and has instructions stored thereon which, when executed by the at least one processor, cause the at least one processor to perform operations including permitting the user to access features in response to receiving an indication that the user is authenticated from the authentication circuit.

These and other implementations can each optionally include one or more of the following features.

In some implementations, the authentication circuit is a field-programmable gate array (FPGA).

In some implementations, the authentication circuit is an application specific circuit (ASIC).

In some implementations, the dynamic power consumption of the authentication circuit is less than 1 mW. In some implementations, the dynamic power consumption of the authentication circuit is less than 500 µW. In some implementations, the dynamic power consumption of the authentication circuit is less than 250 µW. In some implementations, the dynamic power consumption of the authentication circuit is less than 100 µW.

In some implementations, the authentication circuit demonstrates an equal error rate of less than 0.5% and false acceptance rate of less than 0.1% with less than 100 kB of memory and a dynamic power consumption of less than 500 µW.

In some implementations, the authentication circuit demonstrates an equal error rate of less than 0.2% and false acceptance rate of less than 0.01% with less than 100 kB of memory and a dynamic power consumption of less than 100 µW.

In some implementations, the feature extraction circuitry is configured to extract features of the ECG signal using the multiple parallel neural networks to obtain respective feature vectors, particular to each of the neural networks, and concatenate the respective feature vectors to provide the feature vector of the ECG signal.

In some implementations, the noise reduction circuitry is configured to filter the ECG signal with a finite impulse response filter to provide a filtered ECG signal, detect R-peaks in the filtered ECG signal, aligning segments of the ECG signal based on the detected R-peaks in the filtered ECG signal.

In some implementations, the noise reduction circuitry is configured to provide sets of aligned segments of the ECG signal to the feature extraction circuitry, and the feature extraction circuitry is configured to: process each set of aligned segments of the ECG signal by a respective one of the multiple parallel neural networks; extract features from the sets of aligned segments using the multiple parallel neural networks to obtain respective feature vectors, particular to each of the neural networks; and concatenate the respective feature vectors to provide the feature vector of the ECG signal.

In some implementations, each of the sets of aligned segments of the ECG signal are filtered by a respective band-pass filter, each respective band-pass filter having a different pass band.

In some implementations, segments of at least one of the sets of aligned segments are aligned at ECG wave R-peak points, and segments of at least one other of the sets of aligned segments are aligned at ECG wave Q-points.

In some implementations, the noise reduction circuitry is configured to remove outlier data from the ECG data segments.

In some implementations, the noise reduction circuitry is configured to normalize the ECG data segments.

In some implementations, at least one of the multiple parallel neural networks include a compressed layer weight matrix, the compressed layer weight matrix being a sparse approximation of a corresponding non-compressed layer weight matrix. In some implementations, the sparse approximation is a Lasso regression or an orthogonal matching pursuit. In some implementations, only the non-zero weights of the compressed layer weight matrix are stored in memory.

In some implementations, the multiple neural networks each include an input layer and a hidden layer, where particular feature vector of each of the multiple neural networks is an output of the hidden layer of the respective neural network.

In some implementations, the multiple neural networks each include a respective output layer during neural network training, and after training each respective output layer is discarded such that the particular feature vector of each of the multiple neural networks is a direct output of the hidden layer of the respective neural network.

Thus, particular embodiments have been described. Variations, modifications, and enhancements of the described embodiments and other embodiments can be made based on what is described and illustrated. In addition, one or more features of one or more embodiments may be combined. The details of one or more implementations and various features and aspects are set forth in the accompanying drawings, the description, and the claims below.

BRIEF DESCRIPTION OF THE DRAWINGS

FIGS. 3A-3D illustrate graphs of simulated ECG data at various stages of pre-filtering operations.

FIG. 8 is a table showing sparse representation test results for a neural network based biometric authentication system according to implementations of the present disclosure.

DETAILED DESCRIPTION

An ultra-low power ECG-based biometric authentication engine for seamless integration in smart wearable devices with low area and power is described. In implementations, the disclosed engine filters raw digitized ECG signals, performs R-peak detection, removes outliers, and selects PQRST waves from the ECG signal. The selected PQRST waves can be passed through several different finite impulse response (FIR) filters. Outputs of each of the FIR filters wave are passed to one of multiple parallel neural networks (NNs) that have been trained offline. The authentication computes the similarity between the registered user and the current user to authenticate the user. Some implementations of the authentication engine computes a cosine similarity between the registered user and the current user to authenticate the user. To reduce the computation and memory bottleneck, low precision can be selectively applied on different nodes/coefficients/weights without degrading the authentication accuracy. Furthermore, in some implementations neural network weights are compressed by using Lasso regression to find sparse representations of the respective weight matrices of the parallel neural networks. With minimal to no accuracy reduction, the neural network weights can be compressed by 4.2×, which leads to the total memory of the overall system consuming only 36.8 kB. The hardware has been demonstrated on Arria-V FPGA (available from Altera Corporation, San Jose, Calif.) and a 65 nm CMOS prototype ASIC chip and shows equal error rate (EER) of 0.149% and false acceptance rate (FAR) of 0% when false reject rate (FRR) is 5%, which was measured on 32 subjects from an ECG dataset acquired from voluntary individuals. While performing real-time ECG authentication, only 90 μW of dynamic power was consumed.

ECG Authentication System

Figure 1:
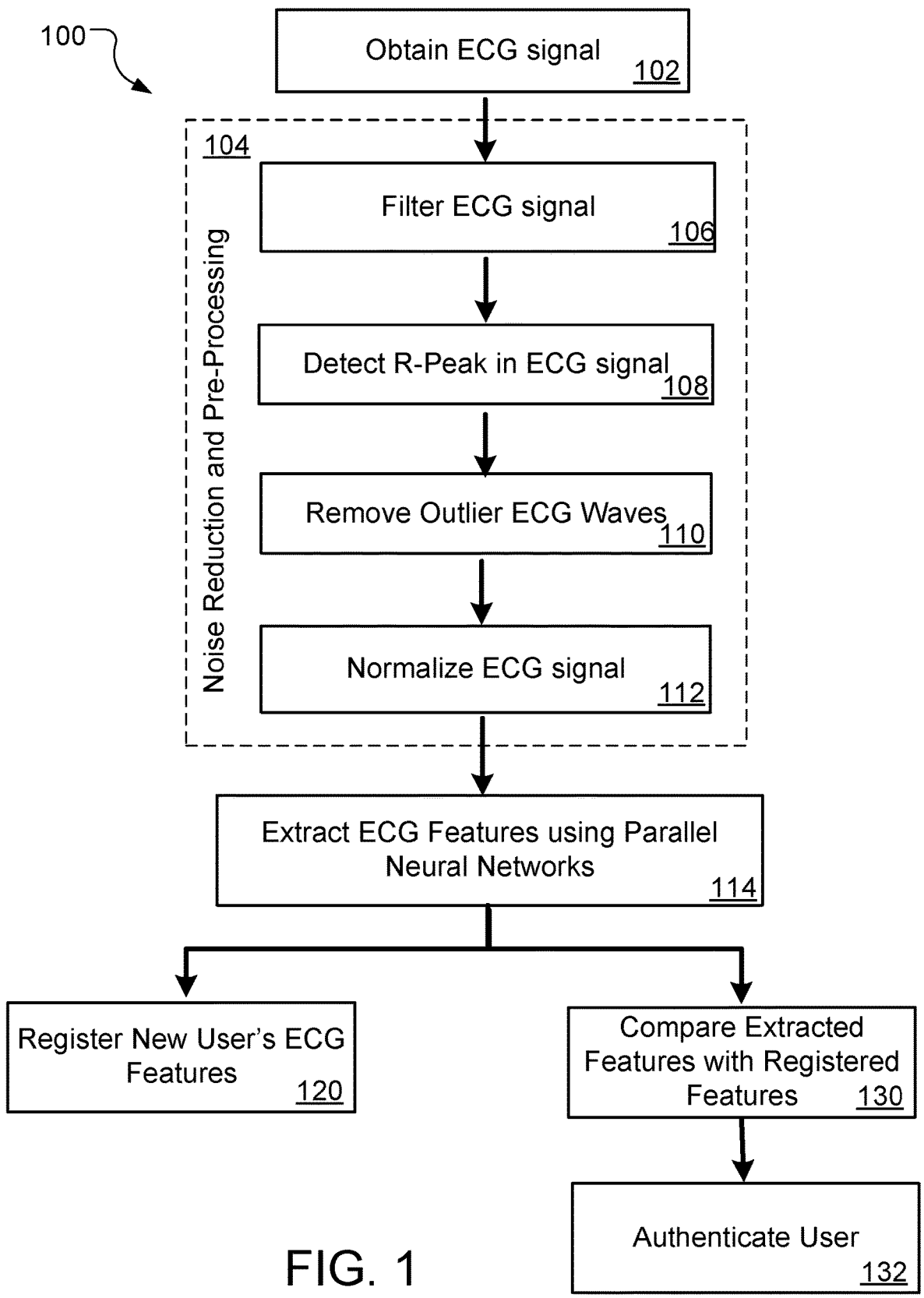
FIG. 1 is a flowchart showing operations in an exemplary ECG authentication process.
Figure 2A:
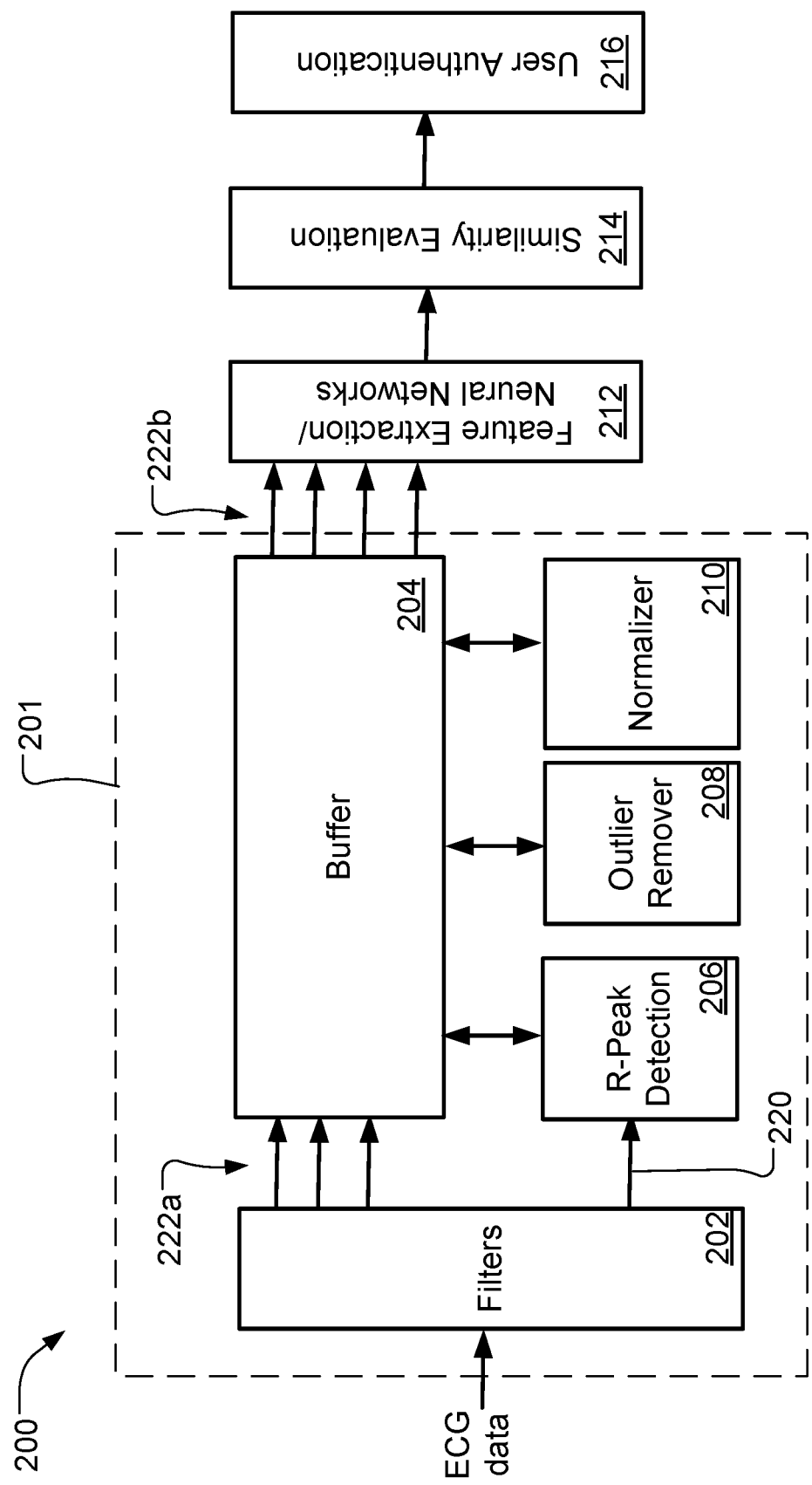
FIG. 2A is a block diagram of an example ECG authentication system according to implementations of the present disclosure.
Figure 2B:
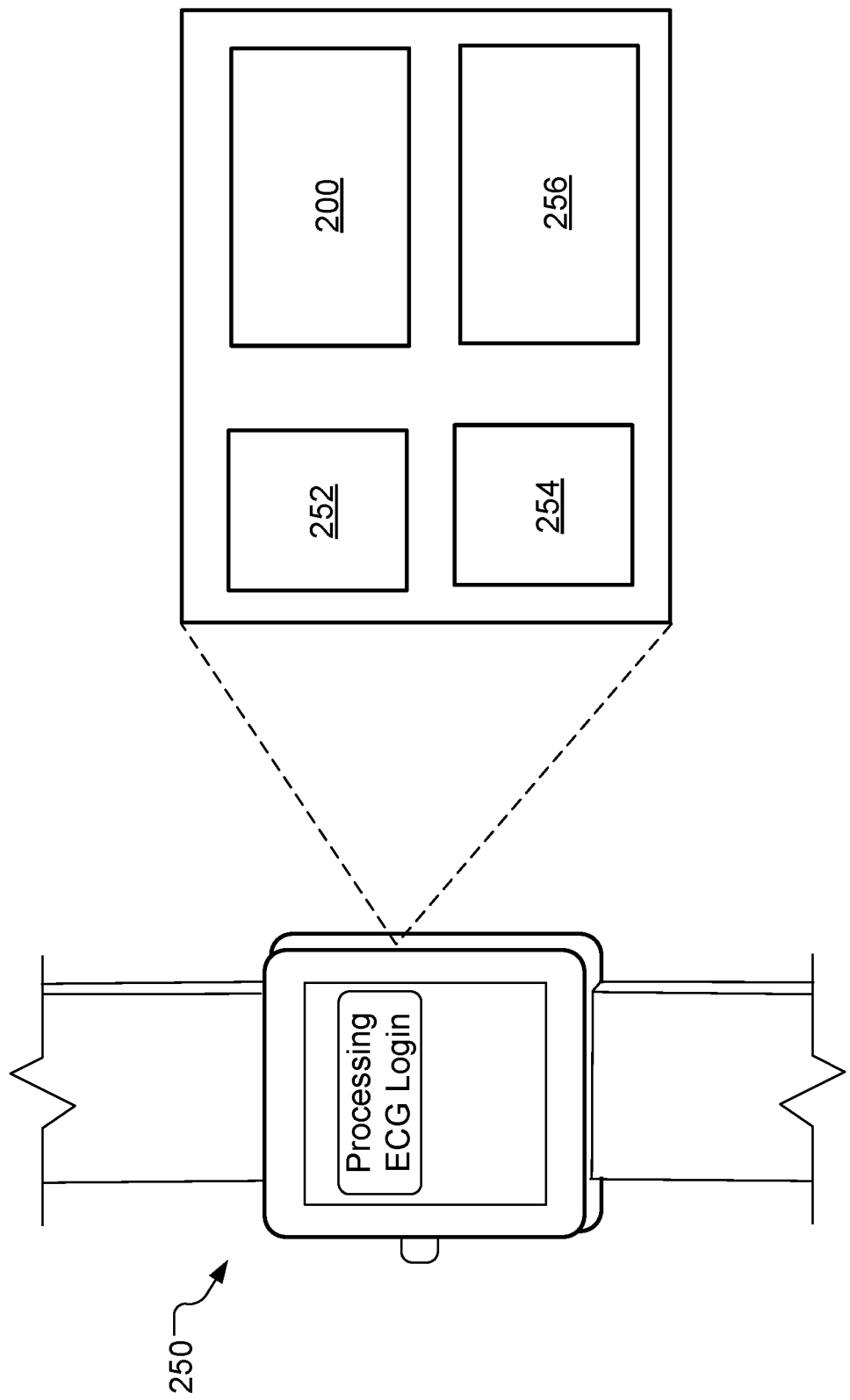
FIG. 2B is a block diagram of an example wearable device that includes the ECG authentication circuitry of FIG. 2A.

FIG. 1 is a flowchart showing operations of an exemplary ECG authentication process 100. Process 100 can be performed by an ECG authentication system such as the ECG authentication system depicted in the block diagram of FIG. 2A and/or the device 250 depicted in FIG. 2B. System 200 can be implemented in hardware (e.g., as integrated circuits, chip-sets, application specific integrated circuits (ASIC) or field programmable logic arrays (FPGA)) or in software (e.g., as software instructions executed by one or more processors). For clarity, system 200 is described herein as being implement as in hardware (e.g., as circuitry of an FPGA), however, in other implementations system 100 can be implemented in other hardware configurations or in software. System 200 includes noise reduction circuitry 201, feature extraction circuitry 212, similarity evaluation circuitry 214, and user authentication circuitry 216. FIG. 2B is a block diagram of an example wearable device 250 that can employ ECG authentication system 200. Wearable device 250 can be, for example, a smart watch, a health monitoring device, a fitness monitoring device, or any type of electronic device in which user authentication security and/or liveness detection may be desired. Although device 250 is described as a wearable device, ECG authentication system 200 may be employed by non-wearable devices for security and/or liveness detection of a user as well, for example, notebook computers, tablet computers, exercise equipment, etc. Device 250 includes ECG authentication system 200, an ECG sensor 252 (or sensors), a processor 256, and data storage 254 (e.g., memory). Data storage 254 and processor 256 store and execute software for perfuming functions of the wearable device 250 (e.g., operating systems, user applications, etc.).

In operation, system 200/device 250 can execute the steps of process 100 to register a user's ECG data or authenticate a previously registered user with the user's ECG signature. Specifically, steps 102-144 and 120 are examples of steps used for user registration. Steps 102-114, 130, and 132 are examples of steps used for user authentication.

Process 100 begins by obtaining ECG data (102). For example, ECG sensor 252 measures and digitizes ECG signals from a user. ECG sensor 252 can be a non-invasive ECG sensor. ECG sensor 252 measures raw ECG signals and digitizes the signals, for example, using a 256 Hz sampling rate analog to digital converter. ECG sensor 252 passes the digitized ECG signal to system 200.

Noise reduction circuitry 201 filters and pre-processes the ECG signal (104). Noise reduction circuitry 201 processes received ECG signals to remove noise and prepare the signals for feature extraction performed by the neural networks. ECG filtering and pre-processing includes four operations: filtering (106), R-peak detection (108), outlier removal (110), and normalization (112). In some instances, ECG pre-processing may omit one or more of these operations, include one or more additional operations, or any combination thereof. In certain instances, the order of operations may be changed.

For example, the noise reduction circuitry 201 can include filters 202, R-peak detection circuitry 206, outlier removal circuitry 208, signal normalizing circuitry 210, and a buffer 204 (e.g., memory). As discussed in more detail below in regard to process 100, the filters 202 of the noise reduction circuitry 208 can include a series of noise reduction filters. The noise reduction filters can include signal isolation filters that are tuned to isolate particular portions of the ECG signal (e.g., particular frequency bands). For example, filters 202 can include a 256-tap FIR noise rejection band pass filter (NRF) with cutoff frequency of 1-40 Hz that is designed to reject both the high frequency noise as well as the DC wandering of the raw ECG signal. Noise reduction filters can include a 40-tap FIR high pass filter (HPF). Noise reduction filters can, optionally, include a cascade of 42-tap FIR band pass filter ("ECG BPF"), differentiator ("ECG DIFF"), and a 11-tap FIR low pass filter ("ECG LPF"). FIGS. 3A-3D illustrate simulated waveforms of the outputs of aforementioned filters. FIG. 2A shows an ECG raw signal; FIG. 2B shows the output of the 42-tap FIR band pass filter; FIG. 2C shows the output of a differentiator; FIG. 2D shows the output of the 11-tap FIR low pass filter together with an R-peak detection threshold that dynamically changes based on R-peak detection. Note that in FIGS. 3A and 3B the QRS wave is labeled in the represented ECG signal. Specifically, the Q, R, and S points of the wave are labeled. In FIG. 3D only the R-peak point is labeled, as the Q and S points have been removed by filtering so as to isolate the R-peak.

In addition to noise reduction filters, filters 202 can also include a set of one or more signal isolation filters. Signal isolation filters can be used to isolate particular portions (e.g., frequency components) of the ECG signal. In one example, the ECG signal is split into multiple (e.g., three) channels 222a and passed through three different signal isolation filters. For example, each of the three signal isolation filters is configured to extract ECG information in a different frequency range, each channel to be processed by a different neural network. In the present example, such signal isolation filters include 256-tap FIR band pass filters with cutoff frequency of 5-40 Hz, 1-40 Hz (two filters), and 5-50 Hz. These three filter types are hereinafter denoted as BPF_5_40, BPF_1_40, and BPF_5_50, respectively. Specifically, in the example described herein, system 100 includes two BPF_1_40 filters.

R-peak detection circuitry 206 detects the R-peaks in the ECG signal. For example, the outputs of LPF, HPF and the four 256-tap FIR BPFs are buffered in different consecutive 64-sample windows. R-peak detection circuitry 206 uses the output of the HPF to determine the maximum peak and minimum peak in a 64-sample window. R-peak detection circuitry 206 uses the output of the LPF to compare with a dynamic threshold in a window to detect the occurrence of an R-peak of ECG wave within that window, which is shown in the waveform of FIG. 2D. R-peak detection circuitry 206 uses R-peak detection algorithms are generally known in the art to detect R-peak points in the ECG signal. When a valid R-peak is detected, R-peak detection circuitry 206 generates and stores sets of ECG signal segments from each of the four signal isolation filters in buffer 204. Based on the location of the detected R-peak point, R-peak detection circuitry 206 aligns the segments in each set at various points of the ECG signal (e.g., the R, S, or Q points). For example, segments in each set are aligned as follows: 160-sample segments from buffer 204 for the output of BPF_5_40 are aligned at R-peak, 50-sample segments from buffer 204 for the output of BPF_1_40 are aligned at R-peak, 50-sample segments from buffer 204 for the output of BPF_5_50 are aligned at Q-point, and 30-sample segments from buffer 204 for the output of BPF_5_50 are aligned at R-peak. Thus, four parallel branches of ECG waves obtained from three types of FIR band pass filters are saved.

Outlier removal circuitry 208 removes outlier waves and data from the ECG signal (e.g., the stored signal segments). For example, after a certain number of ECG waves are detected and collected, outlier removal circuitry 208 discards outliers that are found among the collected ECG waves using an outlier removal algorithm. For example, a QRS wave is defined as an outlier when at least one of the maximum value, minimum value, or cosine distance of the QRS wave is distant from the mean of the maximum, minimum, and cosine distance values of the collected 30 QRS waves, respectively, by more than 50% of the corresponding mean values. To ensure the same number of beats are used in the identification mode, in case an outlier is detected and discarded, new ECG waves are continuously read in until four ECG waves are collected.

Signal normalizing circuitry 210 normalizes the ECG signal (e.g., the stored signal segments). For example, before the four sets ECG signal segments of ECG waves are sent to four corresponding feature extraction neural networks, signal normalizing circuitry 210 normalizes the signals such that the inputs to the networks are bounded within a certain range of values.

Feature extraction circuitry 212 extracts ECG features from the ECG signal using neural networks (114). For example, feature extraction circuitry 212 extracts feature of the ECG signal using multiple parallel neural networks (described below in reference to FIG. 4) to obtain respective feature vectors. Each feature vector is particular to the neural network that produced it. For example, each of the four sets of ECG signal segments (represented by channels 222b) can be provided to one of the parallel neural networks (and as shown graphically in FIG. 4). Each feature vector is representative of features extracted from one of the sets of ECG signal segments provided as input to the respective neural network. After processing by the neural networks, feature extraction circuitry 212 can concatenate the respective feature vectors to provide a comprehensive feature vector for the ECG signal.

Figure 4:
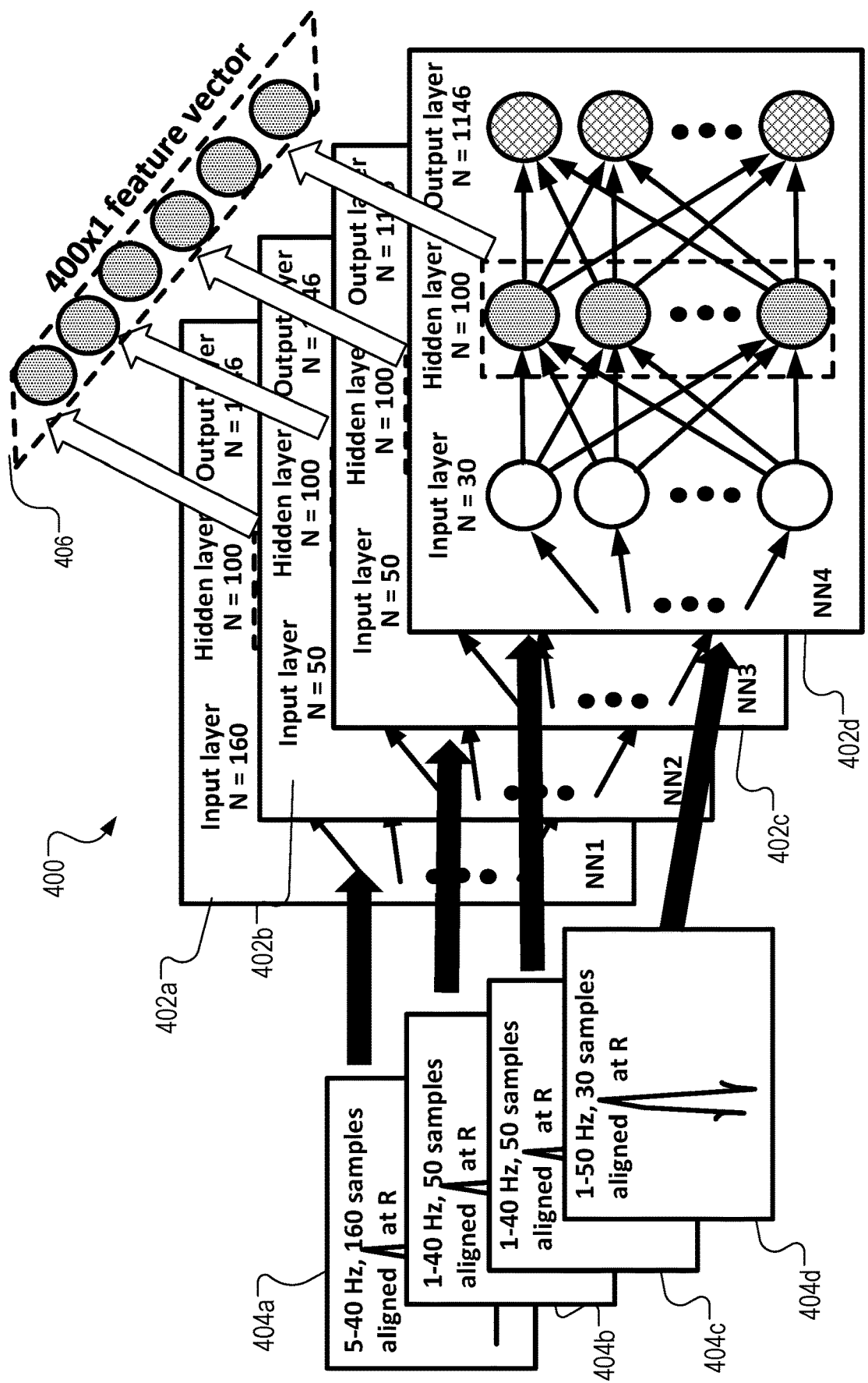
FIG. 4 depicts a block diagram of example parallel neural networks for ECG feature extraction.

FIG. 4 shows a graphical representation 400 of the parallel neural networks 402a-402d. As noted above, feature extraction circuitry 212 provides each set of aligned segments of the ECG signal (denoted as 404a-404d) to one of the parallel neural networks 402a-402d. Each neural network 402a-402d extracts features from a respective set of aligned segments and provides a respective feature vector. For example, each individual feature vector may be a 100×1 element vector. Feature extraction circuitry 212 concatenating the individual feature vectors into a combined 400×1 element feature vector 406 for the ECG signal.

Each neural network 402a-402d includes an input layer, a hidden layer, and an output layer. As discussed below, in some implementations, the output layer is only used for the initial training of the neural networks 402a-402d, and is removed thereafter, for example, to reduce the memory resources used by the neural networks 402a-402d. In such implementations, the feature vectors output by the neural networks 402a-402d are taken directly from the output of the respective hidden layers. Weight matrices for the neural networks 402a-402d may be stored in buffer 204 or in other memory of system 200 or device 250.

In one example, feature extraction circuitry 212 implements four parallel neural networks 402a-402d with input layer, one hidden layer, and output layer designed to capture distinct features from different frequencies and alignment (i.e., aligned at Q versus R). For each neural network 402a-402d, there are 100 hidden layer neurons and 1,146 output layer neurons. The number of input neurons vary from 30 to 160, depending on the number of samples. The activation function of hidden layer is tan h(x).

In the present example, the neural networks 402a-402d are trained as follows. First, a two-layer deep belief network is pre-trained as the initial weights values of neural network. Then, the identity labels of samples are used as the supervision information for fine tuning. After training is done, the intention is to use the hidden layer output as the feature descriptor.

Two loss functions are used for training to improve the overall accuracy: identification loss function and verification loss function. The objective of the identification loss function is to maximize the effect of ECG signal variation from different users on the output nodes. For this, a single network is used. When training with the first individual, only the first output node value is '1', and all the other output node values are '0'. Then error-based back propagation is employed, such that the root-mean-square-error (RMSE) between the actual output layer values and labeled output layer values are minimized. Training is conducted for other individuals in the dataset in a similar fashion. On the other hand, the verification loss function intends to minimize the effect of ECG variation from the same user on the output nodes. This is because variation exists among ECG signals even if they come from the same user. To minimize the effect of this affecting the neural network, two networks that share the same weights are employed to train two different data from the same user.

In the present example, neural network 402a-402d classify ECG signals with feed-forward propagation using the trained weights. Four 100×1 feature vectors are extracted from the hidden layer outputs of the four neural networks and then are concatenated to form a 400×1 feature vector. The average 400×1 feature vector over all valid beats is considered as the final feature vector. Since the hidden layer output is directly used for the feature vector, the weights between the hidden layer and the output layer are not required for classification (only used in training). Accordingly, in such implementations the neural networks each include an input layer and a hidden layer, and feature vectors of each of the multiple neural networks are output directly from the hidden layer of the respective neural networks.

In the case of user registration, system 200 registers the new user's ECG features as a registration feature vector (120). For example, system 200 or device 250 can store the feature vector output from feature extraction circuitry 212 in a user profile. In some implementation, a device 250 may be used by only one user, therefore, only one user registration feature vector may be stored. In other implementations, a device may be used by multiple users, and system 200 or device 250 can store multiple registration feature vectors (e.g., one unique to each registered user) in a user profile for each registered user.

In the case of user authentication, similarity evaluation circuitry 214 comparing the feature vector of the ECG signal with a stored feature vector (e.g., a registration feature vector) of a registered user (130). For example, similarity evaluation circuitry 214 can compare the feature vector output from feature extraction circuitry 212 with a registration feature vector (or multiple registration feature vectors in the case of multiple registered users) using cosine similarity between the new feature vector and the registered feature vector. The cosine similarity can be calculated as follows:

$$csim = \frac{f_{new}^T f_{reg}}{\|f_{new}\|_2 \|f_{reg}\|_2}, \quad (1)$$

where $f_{new}$ is the new feature vector extracted from the current ECG signal and $f_{reg}$ is the registered feature vector.

User authentication circuitry 216 uses the similarity value from similarity evaluation circuitry 214 to authenticate the user (132). For example, user authentication circuitry 216 can authenticate the user in response to determining that a similarity of the ECG feature vector of the ECG signal and the stored ECG feature vector of the registered user exceeds a pre-defined threshold value. For example, user authentication circuitry 216 can compare the computed cosine similarity value against a pre-defined threshold value, to make a decision on identity of the person.

User authentication circuitry 216 sends data that indicates whether a user is authenticated or not to processor 256 of device 250. Device 250 can then permit the user to access one or more features (e.g., applications or unlock the device itself) based on whether the user is properly authenticated.

In some implementations, the system 200 operates in two modes: registration and identification. In the registration mode, the ECG features of an individual may be registered in the system using, for example, 30 beats. In the identification mode, the system extracts the ECG features of the current user using, for example, 4 or 12 incoming beats, and the extracted ECG feature is compared with the registered ECG feature in the system. When the cosine similarity of the two features is above a certain threshold, the user is authenticated to access the given device. Operations of the proposed ECG authentication system may include pre-processing, neural network based feature extraction, and similarity evaluation.

In some implementations, device 250 can use ECG authentication system 200 to continuously or periodically (e.g., at regular or irregular intervals) authenticate a user with little or no input required from the user. Such continuous or periodic authentication may improve the security of such devices and may be particularly advantageous on medical monitoring devices that store sensitive user information (e.g., healthcare information).

Hardware Optimization

In some implementations, hardware design for the ECG authentication system is optimized to minimize the power consumption and memory usage without degrading authentication accuracy. Most blocks in the design are shared between registration and identification mode except for the outlier removal modules due to slightly different signal processing schemes between the two modes.

Low-Precision Representation.

Typically coefficients, nodes, and weights are designed with high precision (i.e., floating point) in the algorithm of ECG signal processing, but such high precision can be too power-hungry and require a large amount of computational resources. Therefore, the system employs a fixed-point design. Instead of having a universal precision across various processing modules, the data widths are optimized for each module individually while checking the final authentication accuracy. The data width of FIR filtering, R-peak detection, outlier removal, normalization, neural network feature extraction and similarity evaluation block were selected as 13-b, 13-b, 11-b, 12-b, 5-b, and 9-b, respectively.

Neural Network Compression.

Neural network based feature extraction typically involves a large amount of computation and memory. However, not all of the weights contribute to the neuron output equally; the values of a large number of trained weights are close to zero. Thus, a sparse approximation of the original weight matrix is implemented such that the approximation error is small enough to avoid recognition accuracy degradation. The sparse approximation may include a weight matrix sparsity enhancement method by Lasso regression based on L2-norm to reduce the hardware implementation cost and power consumption of a trained neural network.

The original weight matrix between the input layer (m neurons) and the hidden layer (n neurons) is denoted as $W_{ori}$ (m×n). Assuming a sufficient number (p) of representative input samples X (p×m) to the neural network, the corresponding weighted sum for the hidden-layer neurons is $Y=XW_{ori}$. W*, a sparse approximation of $W_{ori}$, can be found by solving n Lasso regression problems for each column in the weight matrix. The sparsity can also be controlled by the regularization parameter k, which can trade-off the authentication accuracy. Table I shows memory compression based on Lasso regression.

TABLE I

Memory compression based on Lasso regression.

| | Original weight memory | Compressed weight memory | Memory for address information | Compression ratio |
|---|---|---|---|---|
| NN1 | 100*160*5-b | 100*16*5-b | 100*16*8-b | 3.9X |
| NN2 | 100*50*5-b | 100*5*5-b | 100*5*6-b | 4.6X |
| NN3 | 100*50*5-b | 100*5*5-b | 100*5*6-b | 4.6X |
| NN4 | 100*30*5-b | 100*3*5-b | 100*3*5-b | 5.0X |
| Total | 140 kb | 14.5 kb | 20.3 kb | 4.2X |

Experimental Results

Figure 5:
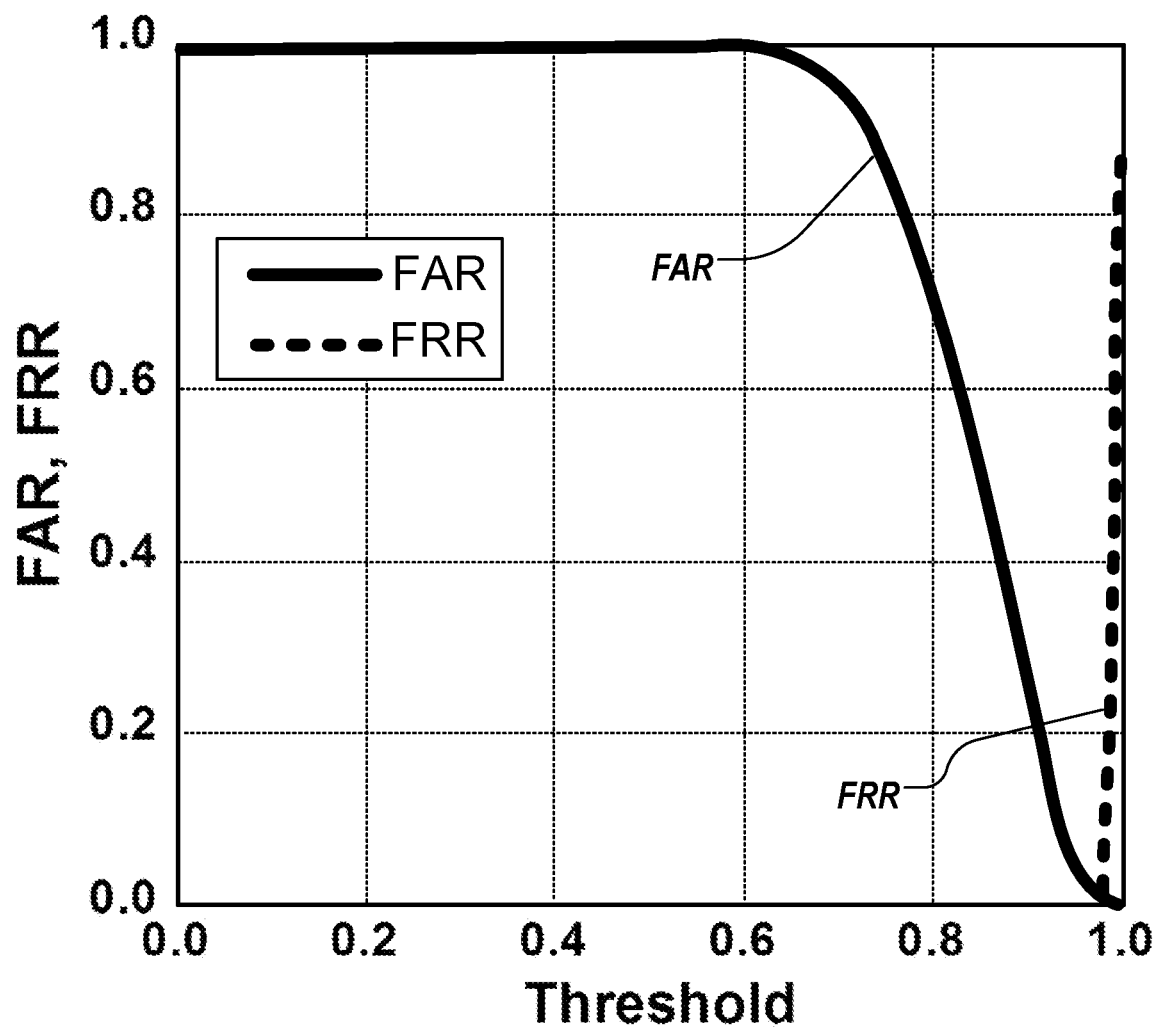
FIG. 5 shows a graph of false acceptance rate (FAR) and false reject rate (FRR) values versus threshold for an example ECG authentication system according to implementations of the present disclosure.

The hardware design demonstrated on an Arria-V FPGA board used a total of 117 k logic elements. The hardware design demonstrated on a 65 nm CMOS prototype ASIC chip used ~5.88 mm² area. Besides the ECG raw data storage used for testing purposes, the total memory usage of the authentication engine was 36.8 kB, out of which only 4.35 kB was attributed to the neural network weight memory, aided by the proposed sparsified memory compression. The authentication accuracy and performance was validated on ECG data of 32 subjects acquired from voluntary individuals. Using 5-b precision on the neural network weights, EER of 0.149% and FAR of 0% at FRR=5% were achieved, and the FAR and FRR values for different threshold values are shown in FIG. 5. With 4-b weight precision, EER modestly degrades to 0.296% and FAR becomes 0.159% at FRR=5%.

Table II shows the power breakdown of different modules in FIG. 3, and the comparison between the original neural network and the compressed neural network. The neural network power is reduced by 2× due to compression, and the overall system power is reduced by 18%.

TABLE II

Dynamic power breakdown of authentication engine implemented in FPGA.

| | Using original trained weights | Using compressed weights |
|---|---|---|
| FIR Filtering | 0.02 mW | 0.01 mW |
| R-peak detection | 0.01 mW | 0.01 mW |
| Outlier removal | 0.00 mW | 0.00 mW |
| Normalization | 0.02 mW | 0.02 mW |
| NN feature extraction | 0.02 mW | 0.01 mW |
| Similarity evaluation | 0.00 mW | 0.00 mW |
| Shared memory | 0.04 mW | 0.04 mW |
| Total | 0.11 mW | 0.09 mW |

In multi-layer neural networks, weight between adjacent layers typically consumes a large amount of memory, which can lead to both area and power overheads in neural network hardware design. Weight memory reduction in neural networks can be advantageous provided the decision-making accuracy of the neural network (e.g., in classifying images, detecting anomalies) is not degraded. As described herein, sparse representation techniques are used to minimize the number of non-zero elements in the weight matrix, and the non-zero weights are stored in memory (compression). Implementations include Lasso regression (L1-norm regularized square error minimization) and L0-norm objective function with sparsity regularization. These sparse representation techniques demonstrate better compression than simple pruning while maintaining comparable decision-making accuracy. The memory compression method is benchmarked for an ECG authentication processor, resulting in minimal degradation accuracy (equal error rate, false acceptance rate) versus the amount of possible memory compression.

In one example using Lasso regression, for each hidden-layer neuron:

$$Z=\tan h(x^T w+b)=\tan h(y+b).$$

Using L1-norm regularized square error minimization, $$\min_{w'}(y-Xw')^T(y-Xw')+\lambda\|w'\|_1$$

where y=Xw, w is the original weight vector, w' is a sparse approximation of w, X is an n×p matrix representing n observations (n=851, p=160/50/50/30). Lasso regression can be applied for each hidden-layer neuron's weight vector. Other types of sparse representation techniques may be used to further compress the memory:

L0-norm minimization with sparsity regularization $$\left(\min_{w'}(y-Xw')^T(y-Xw')+\lambda\|w'\|_0\right)$$

Lp-norm minimization (0<p<1)

$$\left(\min_{\alpha}\|y-X\alpha\|_2^2+\lambda\|\alpha\|_p^p\right)$$

L2-norm minimization $$\left(\min_{\alpha}\|y-X\alpha\|_2^2+\lambda\|\alpha\|_2^2\right)$$

Orthogonal matching pursuit (OMP)
Sparse regression algorithm:

$$A^*x=b$$

Greedy algorithm, iterative, fast

The sparsity of a solution may be controlled. In one exemplary method, the sparsity of a solution is controlled by a method including the following operations. Assume each column in A is normalized. If not, scaling may be performed.
1. Initialize b_res=b.
2. Select the column vector in A which has the largest magnitude of inner product with b_res as the first atom.
3. Update b_res, b_res=b−b_fit, where b_fit is the least square fit of b using selected atoms.
4. Repeat 2 and 3 until K atoms.
5. Obtain a sparsity-K x' via least square fitting b using selected K atoms.

The result may not be the optimal sparsity-K solution (N-P hard), but provides a suitable solution.

Figure 6:
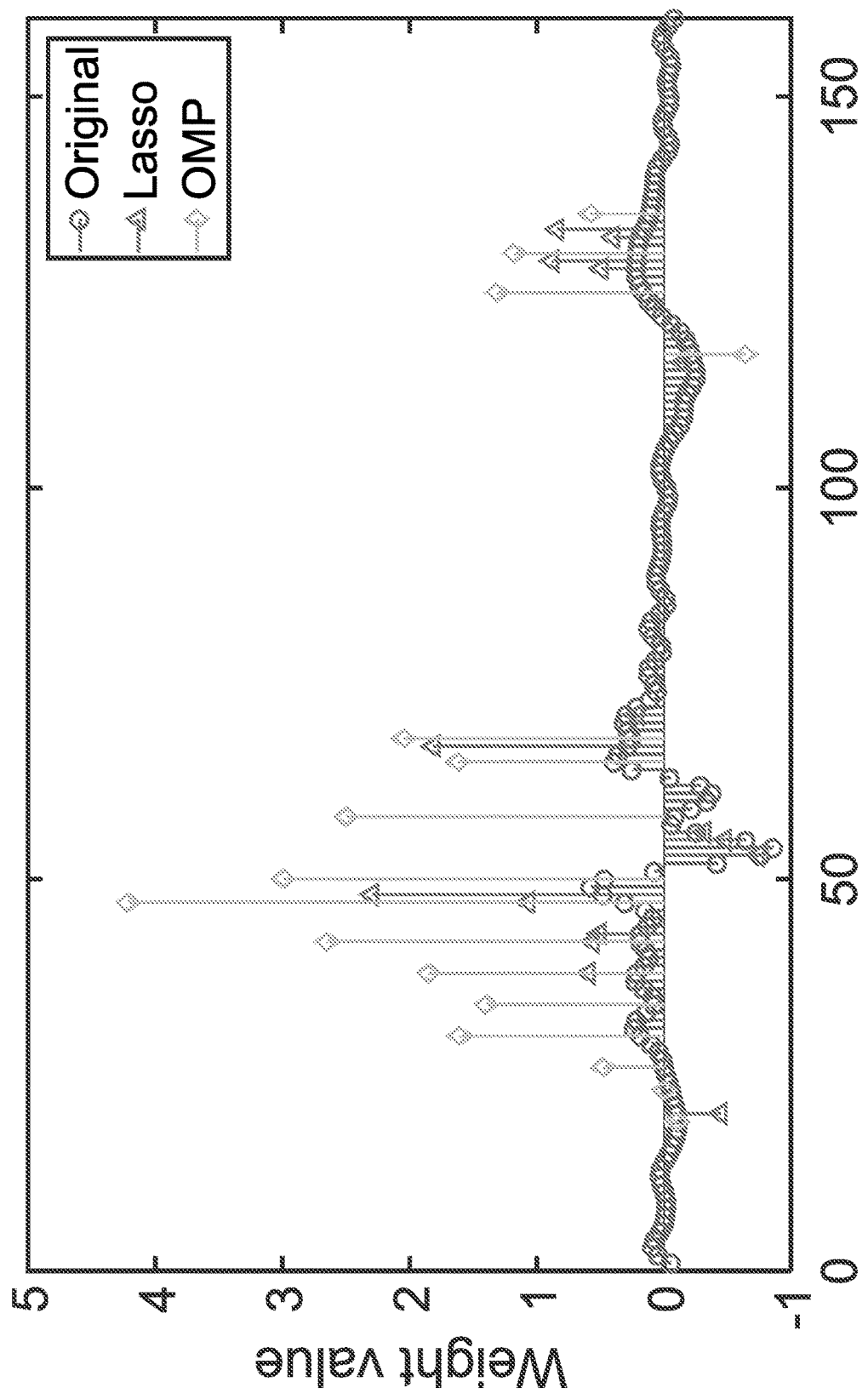
FIG. 6 shows a graph of a sparse representation simulation on trained neural network weights according to implementations of the present disclosure.
Figure 7:
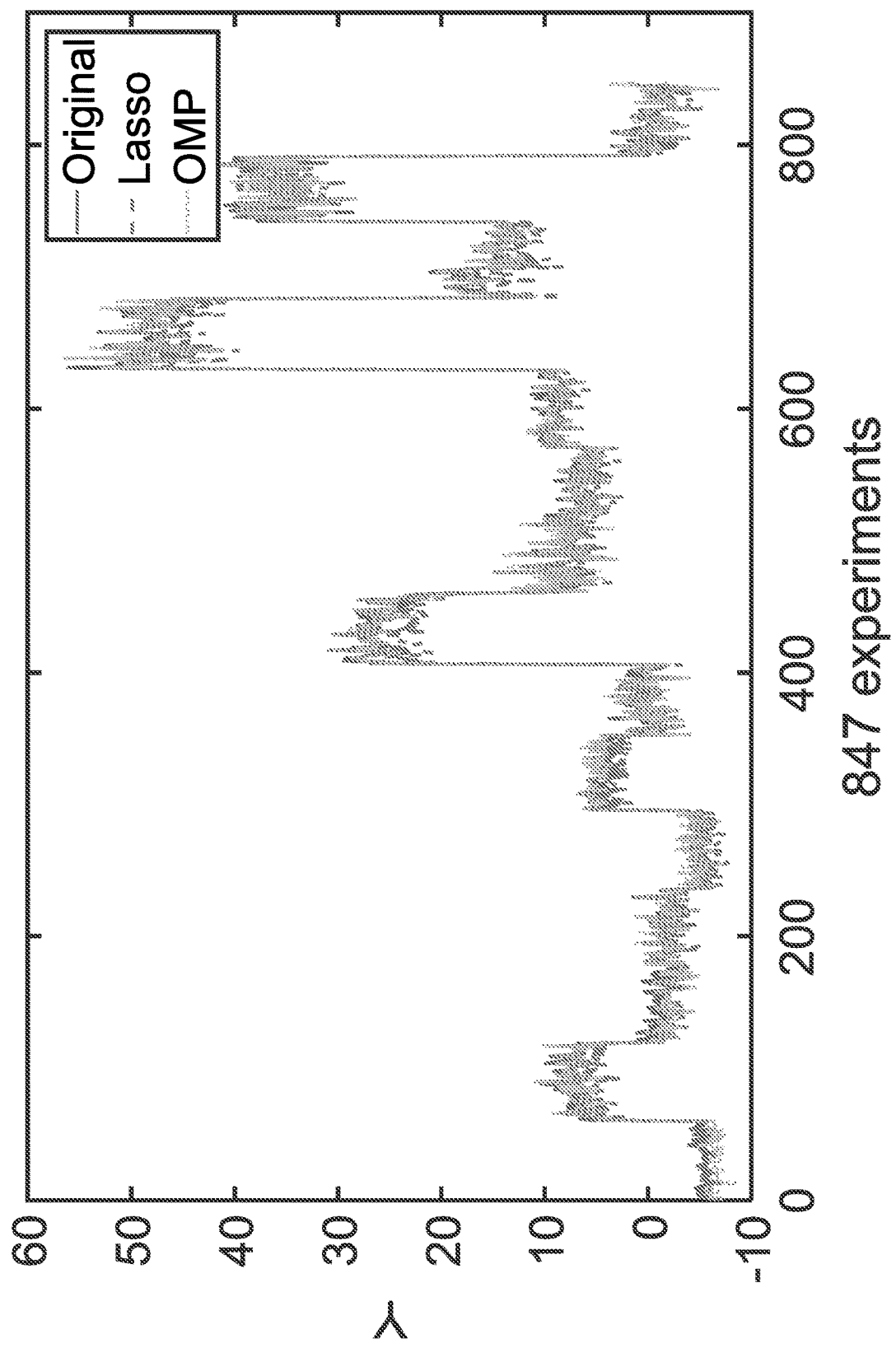
FIG. 7 shows a graph of example neural network simulation data using sparsely represented weight memory according to implementations of the present disclosure.

FIG. 6 shows sparse representation simulation on trained neural networks, with sparsity-16 solutions from Lasso ($\lambda=0.5$) and OMP (K=16). FIG. 7 shows neural network simulation using sparsely represented weight memory for 847 experiments, where Y is the neural network output. The mean squared error for Lasso and OMP is 4.16 and 0.935, respectively.

FIG. 8 is a table showing sparse representation test results for a neural network based biometric system. In FIG. 8, FAR=false acceptance rate; FRR=false rejection rate; ERR=equal error rate when FAR=FRR. Lasso regression results in slightly better FAR then those from simply discarding weights below some thresholds. Selecting $\lambda=0.05$ removes more than 80% weights and still yields the lowest Lasso FAR of 0.588%. Based on these results, advantages of OMP include speed, low approximation error for training, and ease of control for sparsity level. Lasso (basis pursuit) allows global optimization, smaller dynamic range of weights, and ability to overcome overfitting by regularization (may perform better in generalization).

Figure 9:
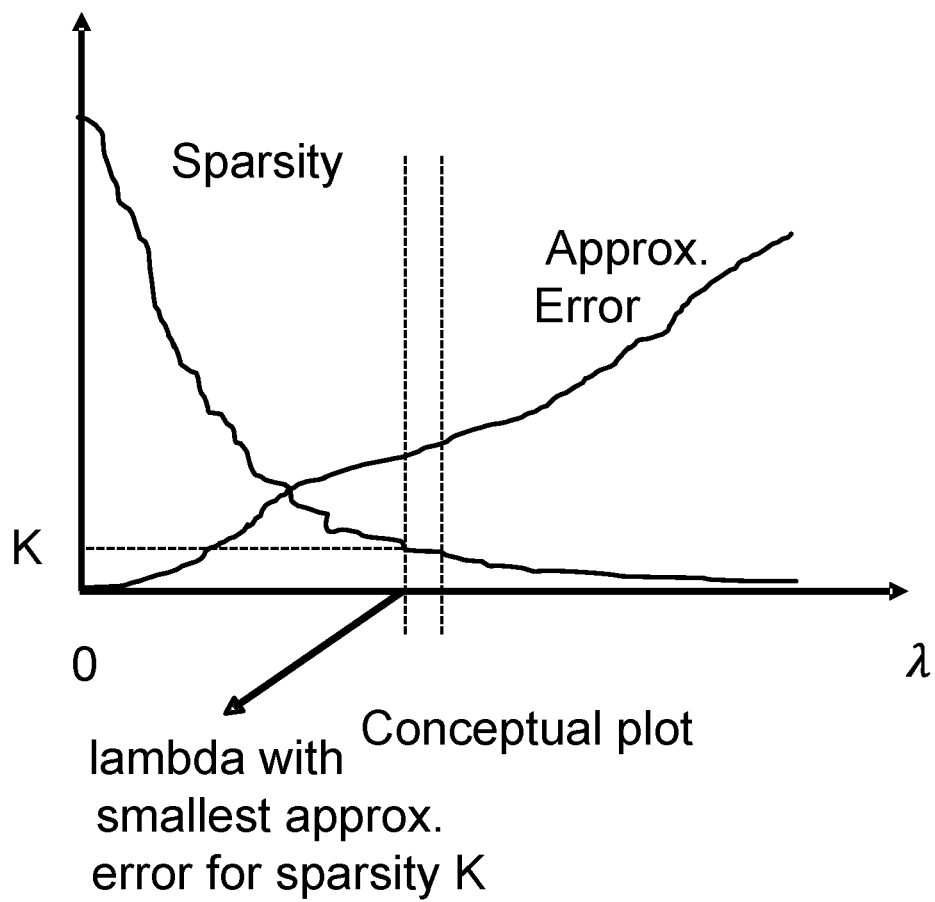
FIG. 9 is a graph that shows sparsity versus λ according to implementations of the present disclosure.

FIG. 9 is a conceptual plot of K versus $\lambda$, for a Lasso regression, showing an increase in approximate error as sparsity decreases. $\lambda$ with the smallest approximation error at sparsity-K level, indicated with the vertical dotted lines, is identified in a binary search that stops when the difference in approximation error is negligible. For example, for sparsity-16, the mean square error decreases from 4.29 to 4.02 when $\lambda$ decreases from 0.5175 to 0.4858.

Figure 10A:
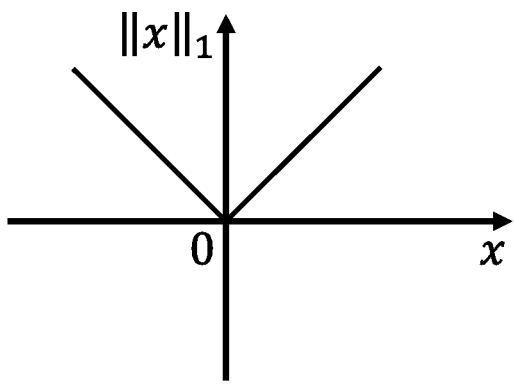
FIG. 10A is a graph that shows L1-norm for a bounded Lasso method.
Figure 10B:
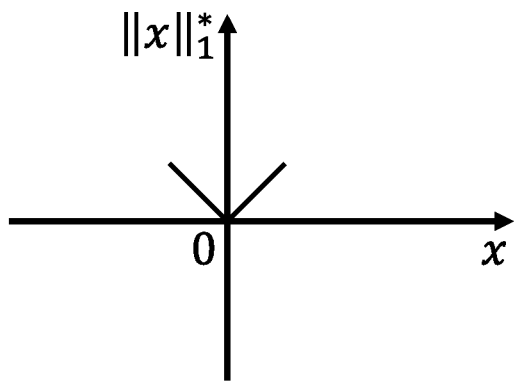
FIG. 10B is a graph that shows a modified L1-norm.

Lasso and OMP may be modified to generate bounded sparse solutions. FIGS. 10A and 10B depict L1-norm and modified L1-norm from a bounded Lasso method. The L1-norm (absolute sum) is modified to add more penalty to larger weights outside the bound while maintaining convexity. In the bounded OMP, after the least fitting step, the highest coefficient is limited to a given bound by scaling, and the scaled least square is fit to update the residual.

Memory compression of sparse data may be achieved in a variety of formats, including coordinate format (COO), compresses sparse row format (CSR), ELL format, bit vector format (BV), and compressed vector format (CBV). In COO, row indices, column indices, and nonzero data are saved. CSR is similar to COO, but instead of saving row indices, only pointers next to row in a pointer array are saved. In the ELL format, every row is extended to maximum length (largest number of non-zeros in a row). ELL is easier to decode (no pointer array is needed), but has a larger storage requirement if the distribution of number of non-zeros of each row is skewed. BV includes a bit-matrix mask with 1 denoting non-zeros and 0 denoting zeros. CBV is similar to BV, but uses fixed-width run-length coding for contiguous sequences of ones and zeros.

Figure 11A:
FIG. 11A shows a greyscale representation of a weight matrix for an example neural network according to implementations of the present disclosure.
Figure 11B:
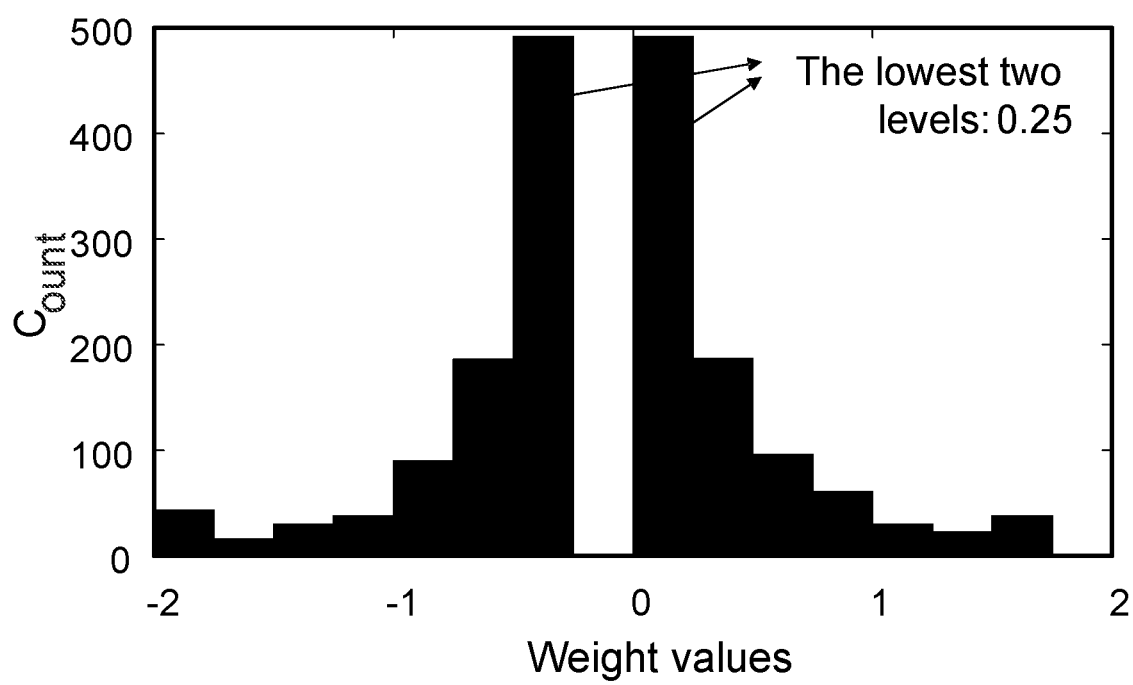
FIG. 11B is a histogram that shows count versus weight values for the matrix of FIG. 11A.

In one example, a weight matrix (Lasso regression, $\lambda=0.05$) was rounded to 4-bit (4-bit precision per weight). FIG. 11A shows a weight matrix for an example neural network (160×100). FIG. 11B shows count versus weight values for the matrix of FIG. 11A. After Lasso regression, the non-zero weight percentage was 11.4%. The two lowest level weights close to zero were pruned, leading to a non-zero weight percentage of 2.72%.

Table III shows total hardware memory requirements for various methods. Based on these results, CBV achieves the highest compression ratio, and CSR achieves similar compression ratio but is easier to decode than CBV.

TABLE III

Total hardware memory requirements for sparsity methods.

| | Data Bits | Extra Bits | Total Bits | Compress Ratio |
|---|---|---|---|---|
| Original | 160x100x4 | 0 | 64000 | 1 |
| COO | 435x4 | 435x(7 + 8) | 8265 | 7.74x |
| CSR | 435x4 | 435x8 + 100x8 | 6020 | 10.6x |
| BV | 435x4 | 160x100 | 17740 | 3.61x |
| CBV* | 435x4 | 360x10 + 435 | 5775 | 11.1x |

*use 10-bit run-length coding for sequences of zeros

Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description. Changes may be made in the elements described herein without departing from the spirit and scope as described in the following claims.

Implementations of the subject matter and the operations described in this specification can be realized in analog or digital electronic circuitry, or in computer software, firmware, or hardware, including the structures disclosed in this specification and their structural equivalents, or in combinations of one or more of them. Implementations of the subject matter described in this specification can be realized using one or more computer programs, i.e., one or more modules of computer program instructions, encoded on computer storage medium for execution by, or to control the operation of, data processing apparatus. A computer storage medium can be, or be included in, a computer-readable storage device, a computer-readable storage substrate, a random or serial access memory array or device, or a combination of one or more of them. Moreover, while a computer storage medium is not a propagated signal; a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field-programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program can, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Devices suitable for storing computer program instructions and data include all forms of non-volatile memory, media and memory devices, including by way of example semiconductor memory devices, e.g., EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing can be advantageous.

What is claimed is:

1. A wearable device comprising:
    an authentication circuit configured to perform electrocardiographic authentication of a user, the authentication circuit comprising:
        an input configured to receive an electrocardiographic (ECG) signal of the user;
        noise reduction circuitry configured to:
            filter the ECG signal with a finite impulse response filter to provide a filtered ECG signal,
            detect R-peaks in the filtered ECG signal, and
            align segments of the ECG signal based on the detected R-peaks in the filtered ECG signal;
        feature extraction circuitry configured to implement multiple parallel neural networks to obtain a feature vector of the ECG signal that represents features extracted from the ECG signal by the neural networks;
        similarity evaluation circuitry configured to determine a cosine similarity of the feature vector of the ECG signal with a stored feature vector of a registered user; and
        authentication circuitry configured to authenticate the user in response to determining the cosine similarity exceeds a pre-defined threshold value;
    at least one processor; and
    a data store coupled to the at least one processor having instructions stored thereon which, when executed by the at least one processor, cause the at least one processor to perform operations comprising:
        permitting the user to access features in response to receiving an indication that the user is authenticated from the authentication circuit,
    wherein the noise reduction circuitry is configured to provide sets of aligned segments of the ECG signal to the feature extraction circuitry, and
    wherein the feature extraction circuitry is configured to:
        process each set of aligned segments of the ECG signal by a respective one of the multiple parallel neural networks,
        extract features from the sets of aligned segments using the multiple parallel neural networks to obtain respective feature vectors, particular to each of the neural networks, and
        concatenate the respective feature vectors to provide the feature vector of the ECG signal.

2. The device of claim 1, wherein the authentication circuit is a field-programmable gate array (FPGA) or an application specific circuit (ASIC).

3. The device of claim 1, wherein a dynamic power consumption of the authentication circuit is less than 1 mW.

4. The device of claim 1, wherein a dynamic power consumption of the authentication circuit is less than 500 µW.

5. The device of claim 1 wherein a dynamic power consumption of the authentication circuit is less than 250 µW.

6. The device of claim 1, wherein the authentication circuit demonstrates an equal error rate of less than 0.5% and false acceptance rate of less than 0.1% with less than 100 kB of memory and a dynamic power consumption of less than 500 µW.

7. The device of claim 6, wherein the authentication circuit demonstrates an equal error rate of less than 0.2% and false acceptance rate of less than 0.01% with less than 100 kB of memory and a dynamic power consumption of less than 100 µW.

8. The device of claim 1, wherein the feature extraction circuitry is configured to:
    extract features of the ECG signal using the multiple parallel neural networks to obtain respective feature vectors, particular to each of the neural networks; and
    concatenate the respective feature vectors to provide the feature vector of the ECG signal.

9. The device of claim 8, wherein at least one of the multiple parallel neural networks comprises a compressed layer weight matrix, the compressed layer weight matrix being a sparse approximation of a corresponding non-compressed layer weight matrix.

10. The device of claim 9, wherein the sparse approximation is a Lasso regression or an orthogonal matching pursuit.

11. The device of claim 9, wherein only non-zero weights of the compressed layer weight matrix are stored in memory.

12. The device of claim 8, wherein the multiple neural networks each comprise an input layer and a hidden layer, and wherein particular feature vector of each of the multiple neural networks is an output of the hidden layer of the respective neural network.

13. The device of claim 12, wherein the multiple neural networks each include a respective output layer during neural network training, and after training each respective output layer is discarded such that the particular feature vector of each of the multiple neural networks is a direct output of the hidden layer of the respective neural network.

14. The device of claim 1, wherein each of the sets of aligned segments of the ECG signal are filtered by a respective band-pass filter, each respective band-pass filter having a different pass band.

15. The device of claim 1, wherein segments of at least one of the sets of aligned segments are aligned at ECG wave R-peak points, and wherein segments of at least one other of the sets of aligned segments are aligned at ECG wave Q-points.

16. The device of claim 1, wherein the noise reduction circuitry is configured to remove outlier data from the segments of the ECG signal.

17. The device of claim 1, wherein the noise reduction circuitry is configured to normalize the segments of the ECG signal.

* * * * *